United States Patent [19]
Olson et al.

[11] Patent Number: 5,342,402
[45] Date of Patent: Aug. 30, 1994

[54] METHOD AND APPARATUS FOR DETECTION AND TREATMENT OF TACHYCARDIA AND FIBRILLATION

[75] Inventors: Walter H. Olson, North Oaks; David K. Peterson, Mounds View, both of Minn.

[73] Assignee: Medtronic, Inc., Minneapolis, Minn.

[21] Appl. No.: 10,906

[22] Filed: Jan. 29, 1993

[51] Int. Cl.$^5$ .......................... A61N 1/00; A61B 5/04
[52] U.S. Cl. .......................... 607/5; 128/705
[58] Field of Search .............. 128/700, 702, 703, 705, 128/5; 607/14, 15

[56] References Cited

U.S. PATENT DOCUMENTS

| | | |
|---|---|---|
| 4,375,817 | 3/1983 | Engle . |
| 4,384,585 | 5/1983 | Zipes . |
| 4,432,375 | 2/1984 | Angel et al. ............... 128/702 |
| 4,548,209 | 10/1985 | Wielders . |
| 4,574,437 | 3/1986 | Segerstad et al. ............ 607/15 |
| 4,577,633 | 3/1986 | Berkovits . |
| 4,587,970 | 5/1986 | Holley . |
| 4,693,253 | 9/1987 | Adams . |
| 4,726,380 | 2/1988 | Vollmann . |
| 4,800,883 | 1/1989 | Winstrom . |
| 4,819,643 | 4/1989 | Menken . |
| 4,880,004 | 11/1989 | Baker, Jr. . |
| 4,880,005 | 11/1989 | Pless . |
| 4,949,719 | 8/1990 | Pless . |
| 4,953,551 | 9/1990 | Mehra . |
| 4,971,058 | 11/1990 | Pless . |
| 5,002,052 | 3/1991 | Halvska ................... 607/14 |
| 5,117,824 | 6/1992 | Keimel . |
| 5,163,427 | 11/1992 | Keimel . |
| 5,181,519 | 1/1993 | Bible ..................... 128/702 |
| 5,205,283 | 4/1993 | Olson .................... 128/705 |

OTHER PUBLICATIONS

"Reliable R-Wave Detection from Ambulatory Subjects", by Nitish V. Thakor, in Biomedical Science Instruments 14:67-72, 1978.

*Primary Examiner*—Lee S. Cohen
*Assistant Examiner*—Marianne Parker
*Attorney, Agent, or Firm*—Reed A. Duthler; Harold R. Patton

[57] ABSTRACT

An apparatus for detecting, identifying and treating tachyarrhythmias. Tachyarrhythmias are detected and identified by the use of overlapping ranges of intervals. Provisional identification of tachyarrhythmia is accomplished by measuring and tracking intervals within two overlapping or adjacent interval ranges. Further classification and identification of tachyarrhythmias is accomplished by determining the relative numbers of intervals within a preceding series falling within a third interval range, overlapping one or both of the interval ranges. In response to identification of the tachyarrhythmia, an appropriate therapy is selected and delivered.

14 Claims, 4 Drawing Sheets

METHOD AND APPARATUS FOR DETECTION AND TREATMENT OF TACHYCARDIA AND FIBRILLATION

BACKGROUND OF THE INVENTION

This invention relates to devices which detect and/or treat tachyarrhythmias (rapid heart rhythms), and more specifically, to mechanisms to distinguish among various tachyarrhythmias and to provide appropriate therapies to treat the identified tachyarrhythmias.

Early automatic tachyarrhythmia detection systems for automatic cardioverter/defibrillators relied upon the presence or absence of electrical and mechanical heart activity (such as intramyocardial pressure, blood pressure, impedance, stroke volume or heart movement) and/or the rate of the electrocardiogram to detect hemodynamically compromising ventricular tachycardia or fibrillation.

In pacemaker/cardioverter/defibrillators presently in clinical evaluation, fibrillation is distinguished from ventricular tachycardia using rate based criteria, In such devices, it is common to specify the rate or interval ranges that characterize a tachyarrhythmia as opposed to fibrillation. However, some patients may suffer from ventricular tachycardia and ventricular fibrillation which have similar or overlapping rates, making it difficult to distinguish low rate fibrillation from high rate tachycardia. In addition, ventricular fibrillation may display R—R intervals which may vary considerably, resulting in intervals that may fall within both the tachycardia and fibrillation rate or interval ranges, or outside both.

Presently available pacemaker-cardioverter-defibrillator arrhythmia control devices, such as the Model 7216A and 7217IB PCD devices available from Medtronic, Inc., employ programmable fibrillation interval ranges and tachycardia detection interval ranges which are adjacent to one another but do not overlap. In the Medtronic devices in particular, the interval range designated as indicative of fibrillation consisting of intervals less than a programmable interval (FDI) and the interval range designated as indicative of ventricular tachycardia consisting of intervals less than a programmable interval (TDI) and greater than or equal to FDI. R—R intervals falling within these ranges are measured and counted to provide a count (VTEC) of R—R intervals falling within the tachycardia interval range and a count (VFEC) of the number intervals, out of a preceding series of a predetermined number (FEB) of intervals, which fall within the fibrillation interval range. VTEC is incremented in response to R—R intervals that are greater than or equal to FDI but shorter than TDI, is reset to zero in response to intervals greater than or equal to TDI and is insensitive to intervals less than FDI. VTEC is compared to a programmed value (VTNID) and VFEC is compared to a corresponding programmable value (VFNID). When one of the counts equals its corresponding programmable value, the device diagnoses the presence of the corresponding arrhythmia, i.e. fibrillation or tachycardia and delivers an appropriate therapy, e.g. anti-tachycardia pacing, a cardioversion pulse or a defibrillation pulse. In addition, the physician may optionally require that the measured R—R intervals meet a rapid onset criterion before VTEC can be incremented and can also optionally require that should a rate stability criterion fail to be met, VTEC will be reset to zero. This detection system has proven effective in distinguishing between fibrillation and ventricular tachycardia so that appropriate therapies may be delivered. However, in rare instances, the detection methodology may require a sequence of a greater number of rapid heart beats than might optimally be desired to determine whether the rapid rhythm is due to fibrillation or tachycardia. Moreover, an improved level of accuracy in classifying rhythms having intervals close to FDI is also believed desirable. In addition, the ability to provide a separate therapy set for fast tachycardias as opposed to slower tachycardias or fibrillation is also desirable.

SUMMARY OF THE INVENTION

One object of the present invention is to distinguish fibrillation from tachycardia at similar rates, using the minimum number of detected heart depolarizations consistent with available accuracy. An additional object of the invention in its preferred embodiments is to distinguish between slow tachycardia, fast tachycardia and fibrillation. In its preferred embodiments, the device takes the form of an implantable pacemaker/cardioverter/defibrillator, and the invention in these embodiments also has the object of providing therapies appropriate to the detected tachyarrhythmia. The disclosed embodiments sense the rhythm of the ventricle and provide therapy for the ventricle, but the invention is also believed to be of value in detecting and treating atrial fibrillation and tachycardias.

In accordance with the present invention, it is realized that because of the randomess of sensed intervals between depolarizations (e.g., R-waves) during fibrillation or because of uncertainties related to a patient's rhythms, sensed cardiac depolarization intervals during fibrillation may have durations which overlap those observed during tachycardias. From the perspective of a device which diagnoses arrhythmias based on measured intervals, intervals defined as indicative of ventricular tachycardia, for example, may in fact be occurring during ventricular fibrillation. The present invention provides a method and apparatus for quickly and accurately classifying the nature of a tachyarrhythmia with intervals near the border between the interval ranges associated with tachycardia and fibrillation.

The disclosed embodiments of the invention operate in the ventricle of the heart and accomplishes identification of such rhythms using a methodology which defines three overlapping interval or rate ranges. Two of the ranges, corresponding generally to tachycardia and fibrillation are adjacent to or overlap one another. A third interval range, corresponding to fast ventricular tachycardia overlaps one or both of the other two interval ranges. Following the provisional detection or identification of ventricular tachycardia or fibrillation, the immediately preceding intervals are examined to determine how many fall within this third interval range. If a predetermined number or percent of the immediately preceding series of intervals fall within this third interval range, fast ventricular tachycardia is detected or identified and the therapy designated for fast ventricular tachycardias is delivered. If less than the predetermined number or percent fall within the fast ventricular tachycardia range, the initially detected arrhythmia (fibrillation or ventricular tachycardia) is confirmed, and the programmed therapy corresponding to the confirmed, detected arrhythmia is delivered.

In one disclosed embodiment of the invention, initial speed of detection or identification of fibrillation or tachycardia is increased by employing a combined count of all measured intervals falling within the interval ranges indicative of fibrillation or tachycardia and then determining whether fibrillation or tachycardia is present by examining the proportions or numbers of recent intervals falling within the tachycardia and fibrillation interval ranges to provide provisional detection or identification of fibrillation or tachycardia. This aspect of the present invention can substantially reduce the number of intervals required to detect fibrillation or tachycardia at rates near the border between the interval ranges associated with tachycardia and fibrillation. This provisional detection or identification of fibrillation or tachycardia may then be further processed as discussed above to distinguish between fast tachycardia and fibrillation or between slow and fast ventricular tachycardia.

BRIEF DESCRIPTION OF THE DRAWINGS

The above and still further objects, features and advantages of the present invention will become apparent from the following detailed description of a presently preferred embodiment, taken in conjunction with the accompanying drawings, and, in which.

DETAILED DESCRIPTION OF THE PREFERRED EMBODIMENT

Figure 1A:
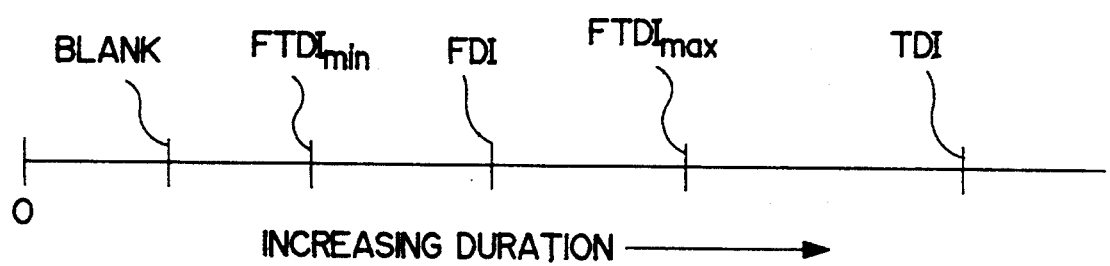
FIG. 1a is an illustration of the detection interval ranges employed in the first preferred embodiment of the present invention.

FIG. 1a is an illustration of the overlapping rate ranges which are employed in a preferred embodiment of the present invention. The range of intervals which are taken as indicative of sinus rhythm are those which are greater than or equal to TDI. The range of intervals taken as indicative of tachycardia includes intervals less than TDI, but greater than or equal to FDI and greater than the device's blanking interval. The range of intervals taken as indicative of fibrillation includes intervals less than FDI. In the first embodiment of the invention, $FTDI_{max}$ is by definition greater than or equal to FDI and $FTDI_{min}$ is by definition less than or equal to FDI. If ventricular tachycardia is provisionally detected, intervals less than $FTDI_{max}$ are taken as indicative of fast ventricular tachycardia. If ventricular fibrillation is provisionally detected, intervals greater than or equal to $FTDI_{min}$ are taken as indicative of fast ventricular tachycardia.

Figure 1B:
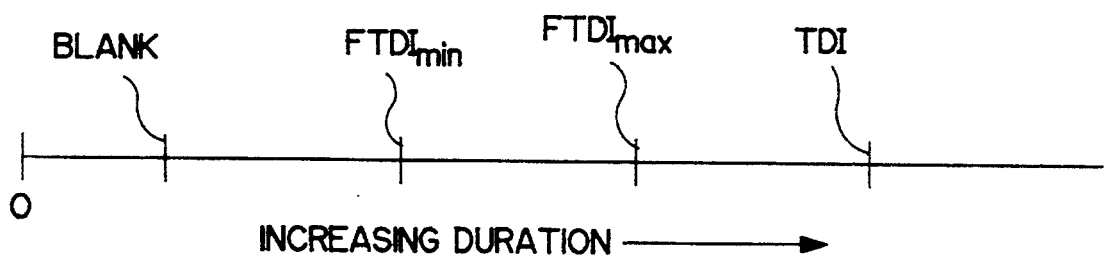
FIG. 1b is an illustration of the detection interval ranges employed in the second preferred embodiment of the present invention.

FIG. 1b is an illustration of the overlapping rate ranges which are employed in second preferred embodiment of the present invention. The range of intervals which are taken as indicative of sinus rhythm are those which are greater than or equal to TDI. $FTDI_{max}$ is by definition greater than or equal to $FTDI_{min}$. The range of intervals taken as indicative of tachycardia includes intervals less than TDI and less than or equal to $FTDI_{min}$. The range of intervals taken as indicative of fibrillation includes intervals less than $FTDI_{max}$ and greater than the device's blanking interval. As in the first embodiment, if ventricular tachycardia is provisionally detected, intervals less than $FTDI_{max}$ are taken as indicative of fast ventricular tachycardia. If ventricular fibrillation is provisionally detected, intervals greater than or equal to $FTDI_{min}$ are taken as indicative of fast ventricular tachycardia.

In the first embodiment of the invention discussed below, using interval ranges corresponding to FIG. 1a, the tachycardia and fibrillation detection criteria discussed above in conjunction with the Medtronic Model 7216 and Model 7217 implantable pacemaker/cardioverter/defibrillators are retained, and used as one set of criteria for provisional detection of tachycardia or fibrillation.

In the first preferred embodiment of the invention, in addition to the fibrillation and tachycardia detection criteria discussed above in connection with the Medtronic Model 7216 and Model 7217, (i.e. VFEC=VFNID or VTEC=VTNID), provisional detection of tachycardia or fibrillation detection may also be accomplished using a combined count of all intervals indicative of tachycardia or fibrillation. This combined count (VFEC+VTEC) is compared to a combined count threshold (CNID). If VTEC+VFEC is equal or greater than CNID, the device checks to see whether VFEC is at least a predetermined number e.g. 6). If so, the device checks to determine how many of a number (e.g. 8) of the immediately preceding intervals are greater or equal to FDI. If a predetermined number (e.g. 8) are greater than or equal to FDI, tachycardia is provisionally detected, otherwise ventricular fibrillation is provisionally detected. The immediately preceding measured intervals are then examined as discussed below to determine whether the initial detection of fibrillation or tachycardia should be confirmed or amended to indicate detection of fast ventricular tachycardia.

In the second preferred embodiment, provisional detection of tachycardia and fibrillation is accomplished using overlapping interval ranges as discussed in conjunction with FIG. 1b, above, but otherwise retaining the basic detection methodology of the Model 7216 and 7217 products referred to above. In this second embodiment, VTEC is incremented by intervals less than TDI and greater than or equal to $FTDI_{min}$, reset by intervals greater than or equal to TDI and unaffected by intervals less than $FTDI_{min}$. VFEC is indicative of the number of intervals out of a preceding series of predetermined number (FEB) of intervals which are less than $FTDI_{max}$.

The present invention, in both disclosed embodiments, is practiced by adding specific new features to the underlying detection methodology of existing prior devices. However, the value of the present invention is not limited to the context of the specific detection criteria disclosed, but is believed workable and valuable in the context of any devices which distinguish between tachycardia and fibrillation using rate or interval based criteria.

As illustrated in FIGS. 1a and 1b, both preferred embodiments of the present invention add a third, fast VT interval range. The third interval range includes intervals which are less than $FTDI_{max}$ if ventricular tachycardia is provisionally detected, and includes intervals greater than or equal to $FTDI_{min}$ if ventricular fibrillation is provisionally detected. Such intervals are taken as indicative of the possibility that a fast ventricular tachycardia is occurring. Both $FTDI_{max}$ and $FTDI_{min}$ are programmable values.

Following provisional detection of tachycardia or fibrillation using either the non-overlapping interval ranges defined by TDI and FDI in the first embodiment or the overlapping interval ranges of the second embodiment, the present invention examines the most recent series of a predetermined number of R—R intervals (e.g. the last 8 intervals) or of a predetermined duration to determine how many of these intervals fall within the fast ventricular tachycardia interval range. The number of intervals in the series may be set less than or equal to VFEC or VTEC and will typically be less than CNID. If a predetermined number of or percentage of sensed intervals within the series fall within the fast ventricular tachycardia range, the rhythm is diagnosed as fast ventricular tachycardia. The number of intervals required to diagnose fast ventricular tachycardia may vary depending on whether ventricular fibrillation or ventricular tachycardia is provisionally detected.

For purposes of the present invention, determining the number or percentage of intervals within the series, which fall within the fast VT interval range may be accomplished by looking to the intervals within the fast VT range, by looking to the intervals outside the fast VT range, or both. For example, if fibrillation was provisionally detected, the device may require that at least 7 or all 8 of the preceding 8 intervals fall within the fast ventricular tachycardia interval range (greater than or equal to $FTDI_{min}$) to detect fast ventricular tachycardia. Equivalently, the device may require that none or no more than one of the preceding 8 intervals fall outside the fast ventricular tachycardia interval range (less than $FFDI_{min}$). Otherwise, detection of ventricular fibrillation is confirmed. If ventricular tachycardia is provisionally detected, the device may only require that at least 1 or 2 of the preceding 8 intervals fall within the fast ventricular tachycardia interval range (less than $FTDI_{max}$) in order to detect fast ventricular tachycardia. Equivalently, the device may require that all 8 or at least 7 of the preceding 8 intervals fall outside the fast ventricular tachycardia interval range (greater than or equal to $FTDI_{max}$). Otherwise, detection of (slow) ventricular tachycardia is confirmed.

In the context of the present invention, it is presumed that each of the possible detected arrhythmias provided by the device will trigger a preset therapy, with the general aggressiveness of the therapies increasing from least aggressive if (slow) ventricular tachycardia is detected to most aggressive if ventricular fibrillation is detected. For example, anti-tachycardia pacing may be employed in response to detection of (slow) ventricular tachycardia, cardioversion may be employed if fast ventricular tachycardia is detected and defibrillation may be employed if fibrillation is detected.

Most currently available devices of the type in which the present invention may be practiced provide for a menu of therapies for each type of detected tachyarrhythmia, with sequentially more aggressive therapies being applied after previous therapies fail to terminate the arrhythmia. In a device incorporating such therapy menus and employing the present invention, the difference between fast and slow tachycardia therapies may lie in the rapidity with which therapies become more aggressive as previously tried therapies fail. For example, the menu of therapies for slow ventricular tachycardia may require three or more attempts at anti-tachycardia pacing prior to providing a high voltage cardioversion shock, the fast ventricular tachycardia menu may provide for only one attempt at anti-tachycardia pacing prior to high voltage cardioversion and the ventricular fibrillation menu may provide only defibrillation shocks of increasing magnitude.

Figure 2:
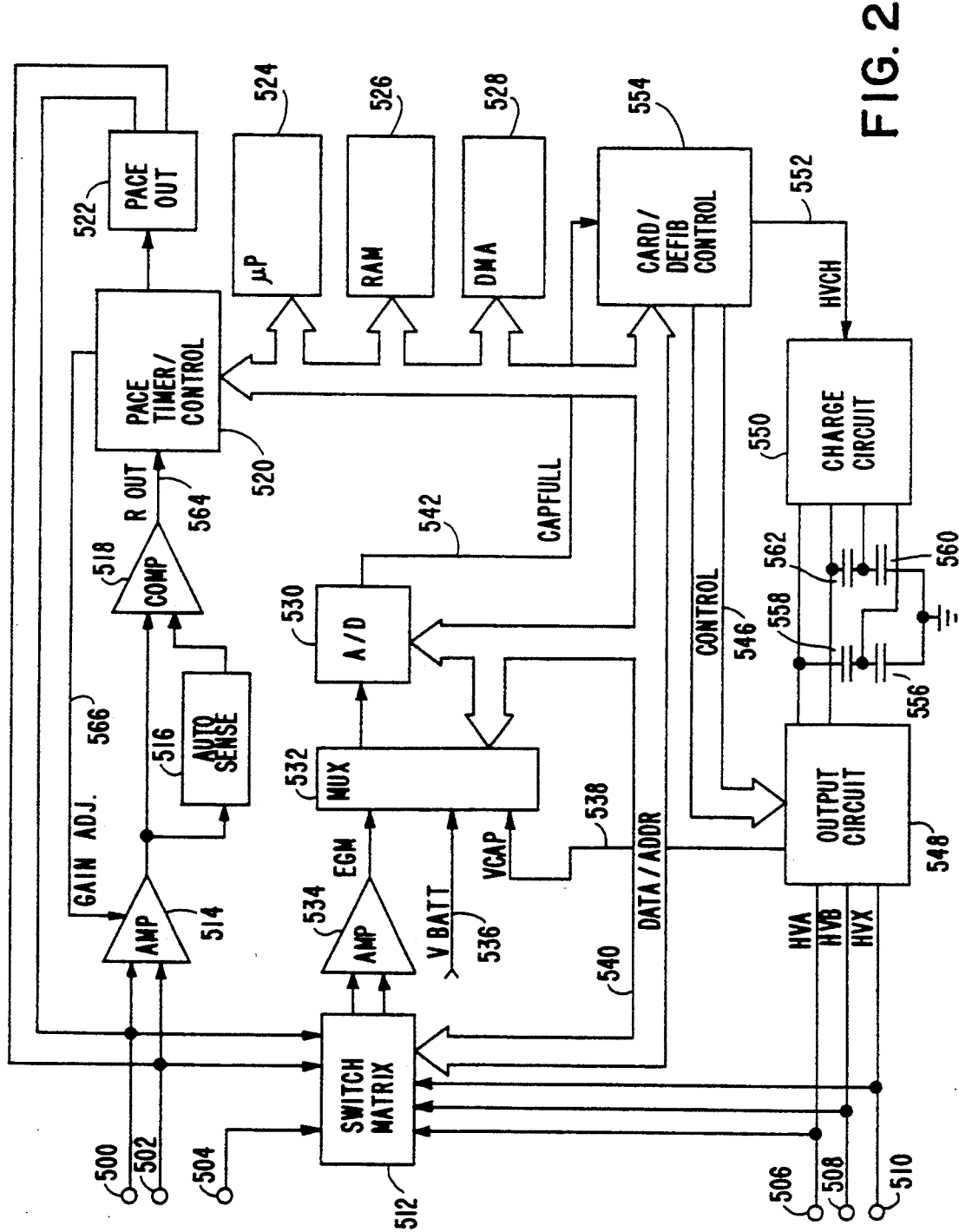
FIG. 2 is a simplified block diagram illustrating the components of a device within which the method and apparatus of the present invention may be implemented.

FIG. 2 is a functional schematic diagram of an implantable pacemaker/cardioverter/defibrillator in which the present invention may usefully be practiced. This diagram should be taken as exemplary of the type of device in which the invention may be embodied, and not as limiting, as it is believed that the invention may usefully be practiced in a wide variety of device implementations, including devices having functional organization similar to any of the implantable pacemaker/defibrillator/cardioverters presently being implanted for clinical evaluation in the United States. The invention is also believed practicable in conjunction with implantable pacemaker/cardioverters/defibrillators as disclosed in prior U.S. Pat. No. 4,548,209, issued to Wielders, et al. on Oct. 22, 1985, U.S. Pat. No. 4,693,253, issued to Adams et al. on Sep. 15, 1987, U.S. Pat. No. 4,830,006, issued to Haluska et al. on May 6, 1989 and U.S. Pat. No. 4,949,730, issued to Pless et al. on Aug. 21, 1990, all of which are incorporated herein by reference in their entireties.

The device is illustrated as being provided with six electrodes, 500, 502, 504, 506, 508 and 510. Electrodes 500 and 502 may be a pair of endocardial electrodes located in the ventricle, mounted to a transvenous lead. Electrode 504 may correspond to a remote, indifferent electrode located on the housing of the implantable pacemaker/cardioverter/defibrillator. Electrodes 506, 508 and 510 may correspond to the large surface area defibrillation electrodes located on ventricular, coronary sinus, superior vena cava or subcutaneous leads, to electrodes located on or part of the device housing or to epicardial defibrillation electrodes.

Electrodes 500 and 502 are shown as hard-wired to the R-wave detector circuit, comprising band-pass filter circuit 514, auto threshold circuit 516 for providing an adjustable sensing threshold as a function of the measured R-wave amplitude and comparator 518. A signal is generated on R-out line 564 whenever the signal sensed between electrodes 500 and 502 exceeds the present sensing threshold defined by the auto threshold circuit 516. As illustrated, the gain on the band pass amplifier 514 is also adjustable by means of a signal from the pacer timing and control circuitry 520 on GAIN ADJ line 566.

The operation of this R-wave detection circuitry may correspond to that disclosed in commonly assigned U.S. Pat. No. 5,118,824, issued to Keimel and incorporated herein by reference in its entirety. However, alternative R-wave detection circuitry such as that illustrated in U.S. Pat. No. 4,819,643, issued to Menken on Apr. 11, 1989 and U.S. Pat. No. 4,880,004, issued to Baker et al. on Nov. 14, 1989, both incorporated herein by reference in their entireties, may also usefully be employed to practice the present invention.

The threshold adjustment circuit 516 sets a threshold corresponding to a predetermined percentage of the amplitude of a sensed R-wave, which threshold decays to a minimum threshold level over a period of less than three seconds thereafter, similar to the automatic sensing threshold circuitry illustrated in the article "Reliable R-Wave Detection from Ambulatory Subjects", by Thakor et al., published in Biomedical Science Instrumentation, Vol. 4, pp. 67-72, 1978, incorporated herein by reference in its entirety.

It is preferable that the threshold level not be adjusted in response to paced R-waves, but instead should continue to approach the minimum threshold level following paced R-waves to enhance sensing of low level spontaneous R-waves associated with tachyarrhythmias. The time constant of the threshold circuit is also preferably sufficiently short so that minimum sensing threshold may be reached within 1-3 seconds following adjustment of the sensing threshold equal to 70-80% of the amplitude of a detected spontaneous R-wave. The invention may also be practiced in conjunction with more traditional R-wave sensors of the type comprising a band pass amplifier and a comparator circuit to determine when the band-passed signal exceeds a predetermined, fixed sensing threshold.

Switch matrix 512 is used to select which of the available electrodes are coupled to band pass amplifier 534. Selection of which two electrodes are so coupled is controlled by the microprocessor 524 via data/address bus 540. Signals from the selected electrodes are passed through band-pass amplifier 534 and into multiplexer 532, where they are converted to multi-bit digital signals by A/D converter 530, for storage in random access memory 526 under control of direct memory address circuit 528. Microprocessor 524 analyzes the digitized EGM signal stored in random access memory 526 to determine the width of the stored R-wave or in conjunction with the tachycardia/fibrillation discrimination function discussed below.

Amplifier 534 may be a broad band pass amplifier, having a band pass extending for approximately 0.5 to 200 hertz. The filtered EGM signal from amplifier 534 is passed through multiplexer 532, and digitized in A-D converter circuitry 530. The digitized EGM data is stored in random access memory 526 under control of direct memory address circuitry 528. Preferably, a portion of random access memory 526 is configured as a looping or buffer memory which stores at least the preceding several seconds of the EGM signal.

The data stored in the buffer memory may be optionally employed to perform R-wave width measurements as disclosed in co-pending U.S. patent application Ser. No. 07/867,931, filed Apr. 13, 1992 by Mader et al, incorporated herein by reference in its entirety and/or to perform the ventricular fibrillation/ventricular tachycardia discrimination function disclosed in allowed U.S. patent application Ser. No. 07/750,679 filed Aug. 27, 1991 by Bardy et al., also incorporated herein by reference in its entirety. However, the present invention may also readily be practiced in devices which do not include such functions.

The occurrence of an R-wave detect signal on line 564 is communicated to microprocessor 524 via data/address bus 540, and microprocessor 524 notes the time of its occurrence. If the width measurement function is activated, microprocessor 524 waits 100 milliseconds or other physician selected interval following the occurrence of the R-wave detect signal, and thereafter transfers the most recent 200 milliseconds or other physician selected interval of digitized EGM stored in the looping or buffer memory portion of the random access memory circuit 526 to a second memory location, where the contents may be digitally analyzed to determine the width of the stored R-wave. The transferred 200 milliseconds of stored EGM corresponds to a time window extending 100 milliseconds on either side of the R-wave detect signal. Window sizes in any case should be sufficient to allow measurement of the width of detected R-waves. Preferably, the window should expire during the blanking period following R-wave detection. For purposes of the present invention, a sampling rate of 256 Hz with a bandpass of 1.5-100 Hz should be sufficient. As discussed below, the width measurement function is intended to discriminate between high rate sinus rhythms and ventricular tachycardias, and is preferably only applied to R-waves that define the endpoint of an R—R interval within the interval range indicative of tachycardia. Either as a criterion for provisional detection of tachycardia, or after confirmed detection of (slow) tachycardia, the device determines whether a predetermined number or proportion of a series of preceding R-waves, the widths of which have been measured, are greater than a preset threshold value (e.g. at least 8 of the preceding 12 measured R-waves). If the width criterion is satisfied, provisional detection of tachycardia or confirmed detection of slow ventricular tachycardia may optionally occur. If the width criterion is not met, the rhythm is diagnosed as rapid sinus rhythm and no therapy is delivered.

Similar to the width measurement function, if the discriminator function is activated, microprocessor 524 waits 100 milliseconds or other physician selected interval following the occurrence of the R-wave detect signal, and thereafter transfers the most recent 200 milliseconds or other physician selected interval of digitized EGM stored in the looping or buffer memory portion of the random access memory circuit 526 to a second memory location, where the contents may be digitally analyzed. The microprocessor 524 identifies the points in time at which the R-wave detect signal occurs and the point in time at which the 200 ms of stored ECG meets a predetermined criterion (e.g. peak slope). These two stored times, hereafter referred to as the first and second "fiducial points". The cumulative variability of the time intervals separating the occurrence of the first and second fiducial points over a series of beats is used to distinguish fibrillation from high rate ventricular tachycardia.

The time interval $\delta$ separating the two fiducial points associated with a single detected depolarization wavefront is measured and stored if the detected depolarization occurs at the end of an R—R interval within the interval range associated with fibrillation. In the context of the present invention, following detection of a rhythm which otherwise would be detected as fast VT, the cumulative variability of the value of $\delta$ over a series of a predetermined number (e.g. 8) of such detected depolarizations is compared to a threshold value set by the physician based on an evaluation of the patient. If the cumulative variability exceeds the threshold, fibrillation is detected. Otherwise, detection of fast ventricular tachycardia is confirmed.

The microprocessor also updates counts related to the R—R intervals previously sensed. The counts, VFEC and VTEC, are incremented on the occurrence of a measured R—R intervals falling within the fibrillation and ventricular tachycardia ranges, respectively, as discussed above. These rate ranges may be defined by the programming stored in the RAM 526.

These counts, along with other stored information reflective of the previous series of R—R intervals such as information regarding the rapidity of onset of the detected short R—R intervals, the stability of the detected R—R intervals, the duration of continued detection of short R—R intervals, the average R—R interval duration and information derived from analysis of stored EGM segments are used to determine whether tachyarrhythmias are present and to distinguish between different types of tachyarrhythmias, as discussed above in conjunction with FIG. 1. Other such detection algorithms for recognizing tachycardias are described in the above cited U.S. Pat. No. 4,726,380, issued to Vollmann, U.S. Pat. No. 4,880,005, issued to Pless et al. and U.S. Pat. No. 4,830,006, issued to Haluska et al., incorporated by reference in their entireties herein. An additional set of tachycardia recognition methodologies is disclosed in the article "Onset and Stability for Ventricular Tachyarrhythmia Detection in an Implantable Pacer-Cardioverter-Defibrillator" by Olson et al., published in *Computers in Cardiology*, Oct. 7–10, 1986, IEEE Computer Society Press, pages 167–170, also incorporated by reference in its entirety herein. However, other criteria may also be measured and employed in conjunction with the present invention.

It is envisioned that onset and stability requirement are optional in a device employing the present invention, and preferably are made available as programmable options, which may be deleted by external programmer command. If included, it is believed preferable that the onset criteria be required to met prior to initiating counting of VTEC, and that once met, the criterion will remain satisfied until detection of tachycardia termination. Thus, onset is not intended to be a detection criteria required for re-detection of tachycardia, following initial detection. The width criterion, if used, should also be understood to preferably used only in initial detection of tachycardia. This reflects a presumption that following initial detection of ventricular tachycardia, absent a proven return to normal heart rhythm (termination detect), subsequent high ventricular rates should be presumed to be ventricular in origin. The stability criterion, on the other hand, is believed to be appropriate for use both in initial detection of tachycardia and in re-detection of tachycardia.

The remainder of the circuitry is dedicated to the provision of cardiac pacing, cardioversion and defibrillation therapies. The pacer timing/control circuitry 520 includes programmable digital counters which control the basic time intervals associated with VVI mode cardiac pacing, including the pacing escape intervals, the refractory periods during which sensed R-waves are ineffective to restart timing of the escape intervals and the pulse width of the pacing pulses. The durations of these intervals are determined by microprocessor 524, and are communicated to the pacing circuitry 520 via address/data bus 540. Pacer timing/control circuitry also determines the amplitude of the cardiac pacing pulses and the gain of band-pass amplifier, under control of microprocessor 524.

During VVI mode pacing, the escape interval counter within pacer timing/control circuitry 520 is reset upon sensing of an R-wave as indicated by a signal on line 564, and on timeout triggers generation of a pacing pulse by pacer output circuitry 522, which is coupled to electrodes 500 and 502. The escape interval counter is also reset on generation of a pacing pulse, and thereby controls the basic timing of cardiac pacing functions, including anti-tachycardia pacing. The duration of the interval defined by the escape interval timer is determined by microprocessor 524, via data/address bus 540. The value of the count present in the escape interval counter when reset by sensed R-waves may be used to measure the duration of R—R intervals, to detect the presence of tachycardia and to determine whether the minimum rate criteria are met for activation of the width measurement function.

Microprocessor 524 operates as an interrupt driven device, and responds to interrupts from pacer timing/control circuitry 520 corresponding to the occurrence of sensed R-waves and corresponding to the generation of cardiac pacing pulses. These interrupts are provided via data/address bus 540. Any necessary mathematical calculations to be performed by microprocessor 524 and any updating of the values or intervals controlled by pacer timing/control circuitry 520 take place following such interrupts.

In the event that a tachyarrhythmia is detected, and an antitachyarrhythmia pacing regimen is desired, appropriate timing intervals for controlling generation of anti-tachycardia pacing therapies are loaded from microprocessor 524 into the pacer timing and control circuitry 520, to control the operation of the escape interval counter and to define refractory periods during which detection of an R-wave by the R-wave detection circuitry is ineffective to restart the escape interval counter. Similarly, in the event that generation of a cardioversion or defibrillation pulse is required, microprocessor 524 employs the counters in timing and control circuitry 520 to control timing of such cardioversion and defibrillation pulses, as well as timing of associated refractory periods during which sensed R-waves are ineffective to reset the timing circuitry.

In response to the detection of fibrillation or a tachycardia requiring a cardioversion pulse, microprocessor 524 activates cardioversion/defibrillation control circuitry 554, which initiates charging of the high voltage capacitors 556, 558, 560 and 562 via charging circuit 550, under control of high voltage charging line 552. The voltage on the high voltage capacitors is monitored via VCAP line 538, which is passed through multiplexer 532, and, in response to reaching a predetermined value set by microprocessor 524, results in generation of a logic signal on CAP FULL line 542, terminating charging. Thereafter, delivery of the timing of the defibrillation or cardioversion pulse is controlled by pacer timing/control circuitry 520. One embodiment of an appropriate system for delivery and synchronization of cardioversion and defibrillation pulses, and controlling the timing functions related to them is disclosed in more detail in allowed, commonly assigned U.S. patent application Ser. No. 07/612,761, by Keimel, for an Apparatus for Detecting and Treating a Tachyarrhythmia, filed Nov. 15, 1990 and incorporated herein by reference in its entirety. However, any known cardioversion or defibrillation pulse generation circuitry is believed usable in conjunction with the present invention. For example, circuitry controlling the timing and generation of cardioversion and defibrillation pulses as disclosed in U.S. Pat. No. 4,384,585, issued to Zipes on May 24, 1983, in U.S. Pat. No. 4949719 issued to Pless et al., cited above, and in U.S. Pat. No. 4,375,817, issued to Engle et al., all incorporated herein by reference in their entireties may also be employed. Similarly, known Circuitry for controlling the timing and generation of anti-tachycardia pacing pulses as described in U.S. Pat. No. 4,577,633, issued to Berkovits et al. on Mar. 25, 1986, U.S. Pat. No. 4,880,005, issued to Pless et al. on Nov. 14, 1989, U.S. Pat. No. 7,726,380, issued to Vollmann et al. on Feb. 23, 1988 and U.S. Pat. No. 4,587,970, issued to Holley et al. on May 13, 1986, all of which are incorporated herein by reference in their entireties may also be used.

In modern pacemaker/cardioverter/defibrillators, the particular anti-tachycardia and defibrillation therapies are programmed into the device ahead of time by the physician, and a menu of therapies is typically provided. For example, on initial detection of tachycardia, an anti-tachycardia pacing therapy may be selected. On re-detection of tachycardia, a more aggressive anti-tachycardia pacing therapy may be scheduled. If repeated attempts at anti-tachycardia pacing therapies fail, a higher level cardioversion pulse therapy may be selected thereafter. Prior art patents illustrating such pre-set therapy menus of antitachyarrhythmia therapies include the above-cited U.S. Pat. No. 4,830,006, issued to Haluska, et al., U.S. Pat. No. 4,727,380, issued to Vollmann et al. and U.S. Pat. No. 4,587,970, issued to Holley et al. The present invention is believed practicable in conjunction with any of the known anti-tachycardia pacing and cardioversion therapies, and it is believed most likely that the invention of the present application will be practiced in conjunction with a device in which the choice and order of delivered therapies is programmable by the physician, as in current implantable pacemaker/cardioverter/defibrillators.

In addition to varying the therapy delivered following a failed attempt to terminate a tachyarrhythmia, it is also known that adjustment of detection criteria may be appropriate. For example, adjustment may comprise reducing the number of intervals required to detect a tachyarrhythmia to allow a more rapid re-detection or by changing the interval ranges to bias detection towards detection of ventricular fibrillation, for example as disclosed in U.S. Pat. No. 4,971,058, issued to Pless et al and incorporated herein by reference in its entirety.

In the present invention, selection of the particular electrode configuration for delivery of the cardioversion or defibrillation pulses is controlled via output circuit 548, under control of cardioversion/defibrillation control circuitry 554 via control bus 546. Output circuit 548 determines which of the high voltage electrodes 506, 508 and 510 will be employed in delivering the defibrillation or cardioversion pulse regimen, and may also be used to specify a multi-electrode, simultaneous pulse regimen or a multi-electrode sequential pulse regimen. Monophasic or biphasic pulses may be generated. One example of circuitry which may be used to perform this function is set forth in U.S. Pat. No. 5,163,427, issued to Keimel, incorporated herein by reference in its entirety. However, output control circuitry as disclosed in U.S. Pat. No. 4,953,551, issued to Mehra et al. on Sep. 4, 1990 or U.S. Pat. No. 4,800,883, issued to Winstrom on Jan. 31, 1989 both incorporated herein by reference in their entireties, may also be used in the context of the present invention. Alternatively single monophasic pulse regimens employing only a single electrode pair according to any of the above cited references which disclose implantable cardioverters or defibrillators may also be used.

Figure 3A:
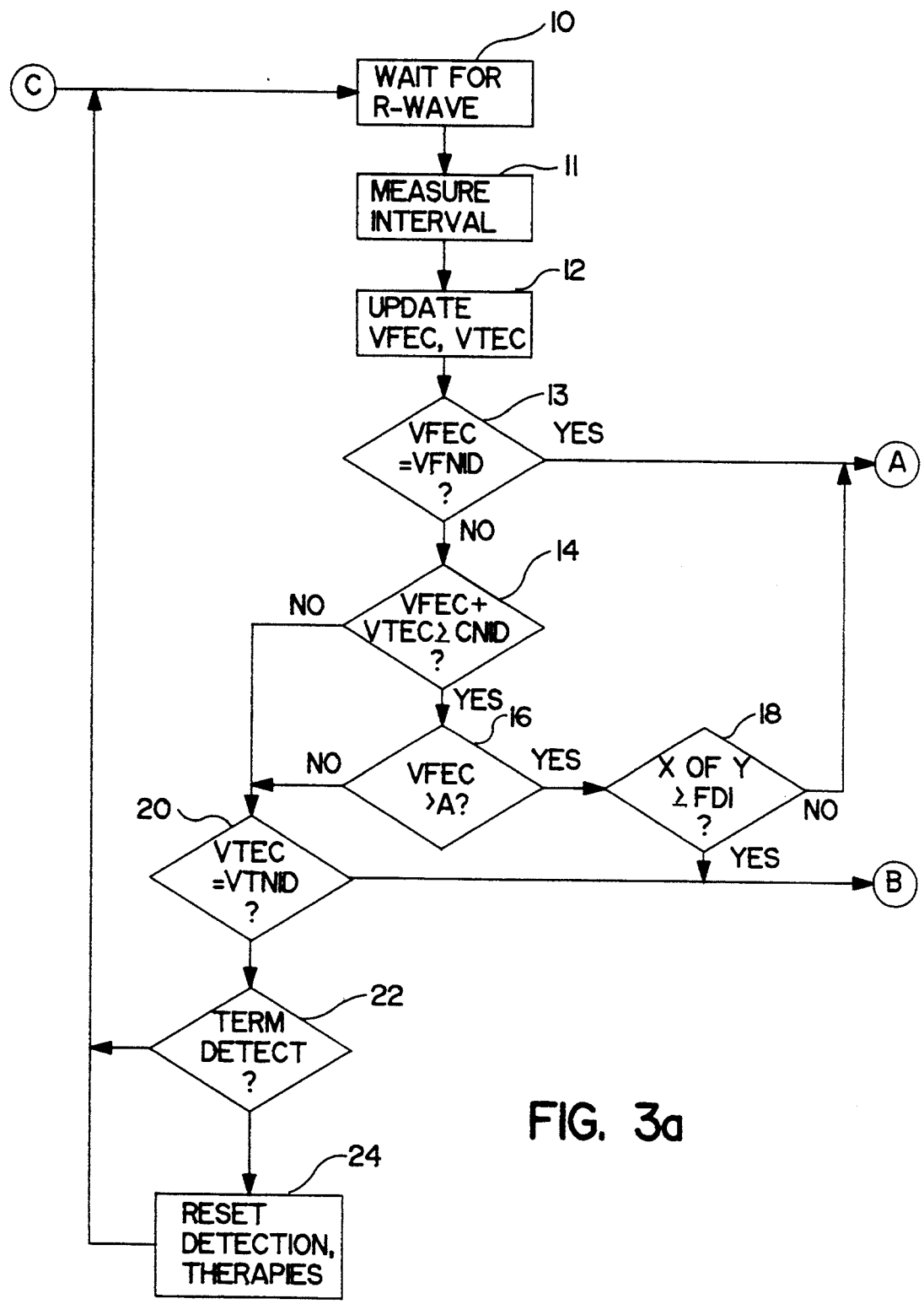
FIGS. 3a and 3b are simplified flow chart diagrams illustrating the functional operation of the preferred embodiments of the present invention.
Figure 3B:
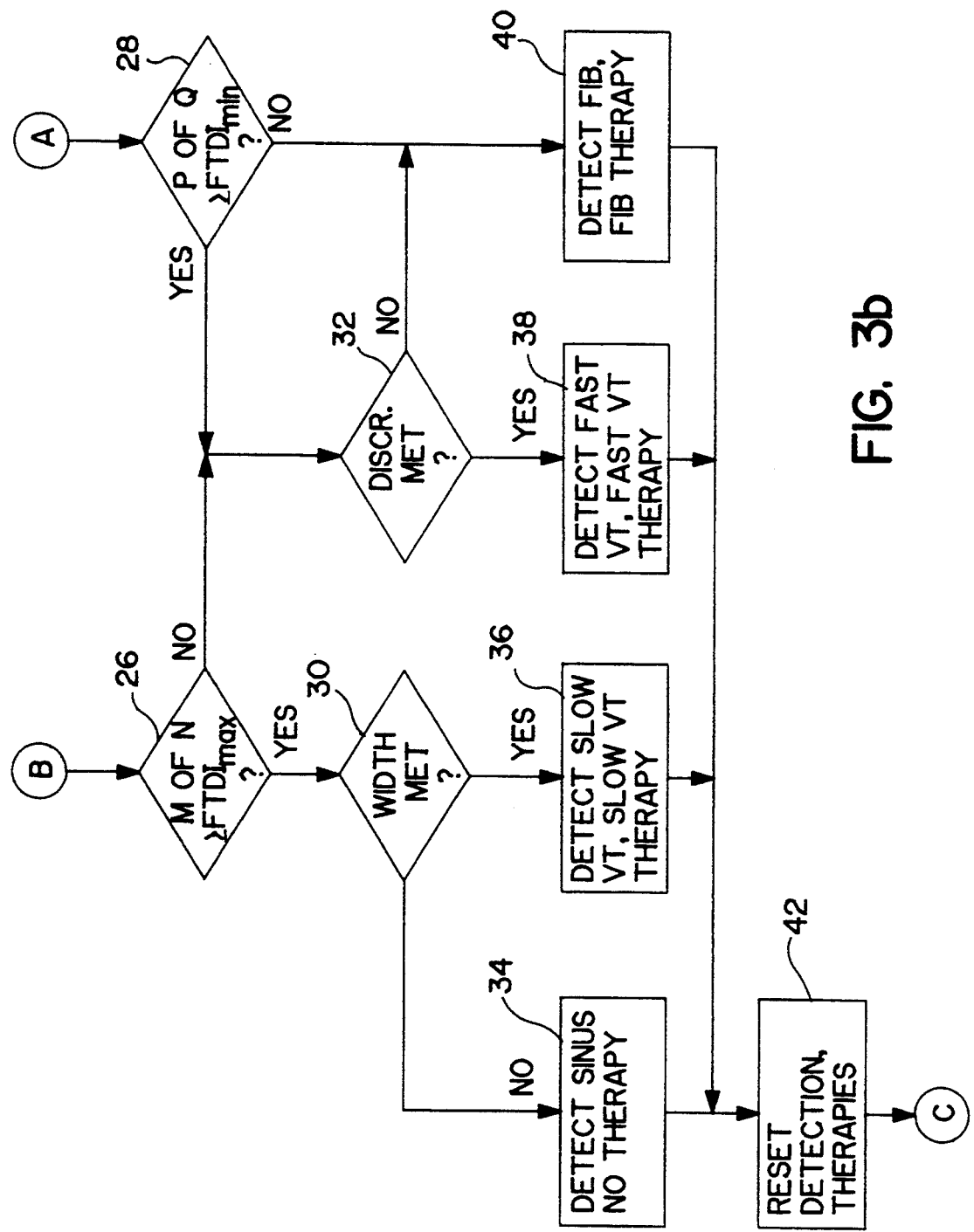

FIGS. 3a and 3b are a functional flow chart illustrating the operation of the first preferred embodiment of the present invention, as embodied in the context of a device illustrated in FIG. 2. In FIG. 3a, it should be understood that the device may be in general operating as a demand pacemaker, and that the analysis undertaken takes place in response to the occurrence of sensed or paced depolarizations of the heart. At 10, the device is awaiting the occurrence of the next subsequent R-wave. Upon occurrence of the R-wave, the processes and functions described above related to storing the time of occurrence of the R-wave, measuring the R—R interval preceding the R-wave and, if appropriate, analyzing the stored digital wave-form associated with the R-wave are all undertaken at 11. At 12, the VTEC and VFEC counts are updated.

At 13, device checks to determine whether VFEC equals VFNID. If so, fibrillation is provisionally detected. If not, the sum of VFEC and VTEC is compared to CNID at 14. If their sum is equal to or greater than CNID, the device checks at 16 to determine whether VFEC is greater than a predetermined number, for example 5. If so, the device checks at 18 to see whether a predetermined number X of the preceding Y R—R intervals (e.g. at least 7 or all 8 out of the preceding 8 intervals) are greater than or equal to FDI. If so, tachycardia is provisionally detected, if not, fibrillation is provisionally detected.

In the event that either the sum of VFEC+VTEC is less than CNID at 14 or VFEC is less than or equal to A at 16, the device checks at 20 to determine whether VTEC equals VTNID. If so, ventricular tachycardia is provisionally detected, if not, the device checks at 22 to determine whether a tachyarrhythmia has previously been detected and whether the previous series of R-waves indicate termination of the previously detected tachyarrhythmia. Detection of termination of tachycardia or fibrillation may be accomplished by means of detection of a predetermined number (e.g. 8) of sequential R—R intervals indicative of normal heart rate. Normal heart rate may be defined as R—R intervals greater than or equal to TDI. If termination is detected, detection criteria and anti-arrhythmia therapy menus are reset at 24, as described above in conjunction with FIG. 2. If not, the device simply waits for the next R-wave at 10.

In the event that the second preferred embodiment is to be practiced, the flow chart of FIG. 3a remains applicable, with the exception that the combined count provisional detection function of blocks 14, 16 and 18 is not used. In this case, in response to a failure to provisionally detect fibrillation at 13, the device proceeds directly to block 20, to determine whether ventricular tachycardia can be provisionally detected.

In the event that tachycardia is provisionally detected, at 18 or 20, the device checks at 26 (FIG. 3b) to determine whether a predetermined number M of the preceding N intervals (e.g., 7 or 8 of the preceding 8) are greater than or equal to $FTDI_{max}$ and thus outside the fast VT interval range (i.e. only one or none of the intervals are within the fast VT range). If not, a fast ventricular tachycardia is detected and fast ventricular tachycardia therapy is delivered at 38. If so, the device may simply proceed to deliver slow VT therapy at 36. However, as illustrated, the width criteria may optionally be applied at 30. In this case, application of the width criteria is directed towards distinguishing a slow ventricular tachycardia from a rapid sinus rhythm. If the width criterion is met, as discussed above, a slow VT therapy is delivered at 36. If not, the device detects a rapid sinus rhythm and no therapy is delivered at 34.

In the event that fibrillation is provisionally detected at 13 or 18, the device checks at 28 to determine whether a predetermined number P out of the preceding Q intervals (e.g., 7 or 8 of the preceding 8) are greater than or equal to FTDI$_{min}$ and thus within the fast VT interval range. If not, the device confirms the detection of fibrillation and proceeds directly to deliver ventricular fibrillation therapy at 40. If so, the device may detect fast VT and proceed directly to deliver the fast ventricular tachycardia therapy at 38. However, as illustrated, the device may also optionally check at 32 to determine whether the criterion established by the ventricular tachycardia/ventricular fibrillation discrimination function is met. If the criterion is not met, ventricular fibrillation is detected and fibrillation therapy is delivered at 40. If the criterion is met, fast ventricular tachycardia is confirmed and fast VT therapy is delivered at 38. After delivery of therapy at 36, 38 or 40 or following inhibition of anti-tachycardia therapy at 34, the therapy menus and detection criteria are reset at 42 to reflect the preceding detection of tachyarrhythmia and delivery of tachyarrhythmia therapy, as discussed above in conjunction with FIG. 2. The device then returns to block 10, awaiting the next successive R-wave, so that it may determine whether the tachyarrhythmia has been terminated, persists, or has changed to another type of tachyarrhythmia.

The above disclosed embodiment illustrates the case in which all functions of the preferred embodiment of the present invention are activated. However, it is to be expected that in commercially released devices, the physician will be provided with the opportunity to selectively enable and disable individual portions of the tachyarrhythmia detection and classification functions illustrated. For example, the physician may wish to disable the detection of fast ventricular tachycardia from a provisional detection of ventricular fibrillation, a provisional detection of ventricular tachycardia or both. The physician may program the device to allow detection of fast VT only following provisional detection of ventricular fibrillation. In such case, FTDI$_{max}$ may be st equal to FDI. In response to provisional detection of ventricular tachycardia, the device would either proceed directly to delver a slow ventricular tachycardia therapy 36 following provisional ventricular tachycardia detection, or might optionally apply the width criteria at 30 as prerequisite to delivery of slow ventricular tachycardia therapy. Alternatively, the physician may program the device to allow detection of fast VT only following provisional detection of ventricular tachycardia. In such case, FFDI$_{min}$ in may be set equal to FDI. In response to a provisional detection of ventricular fibrillation, the device would proceed directly to delivery of ventricular fibrillation therapy at 40 in FIG. 3*b*.

Disabling all fast ventricular tachycardia detection and setting both FTDI$_{max}$ and FTDI$_{min}$ to be equal FDI in effect returns the interval ranges to those that would be present in the Model 7216 and Model 7217, discussed above, and eliminates the fast ventricular tachycardia interval range entirely. However, increased speed of detection of ventricular fibrillation or tachycardia would still be provided by the combined count detection methodology discussed above.

As such, the invention as illustrated provides for a wide flexibility in its use, and allows the physician to tailor the detection criteria to the needs of the specific patient in whom the device is to be implanted. In conjunction with this, it should also be kept in mind that all numerical variables and counts illustrated in FIG. 3*b* may also be subject to programming and control by the physician, in addition to the boundaries of the various interval ranges.

While the preferred embodiment of the device takes the form of a microprocessor controlled device as illustrated in FIG. 2, in which the various functional steps illustrated in FIGS. 3*a* and 3*b* would be implemented in the form of software, the invention may equally well be practiced in the form of a dedicated, full custom digital integrated circuit or, even in the form of an analog circuit, employing analog values as substitutes for the digital values disclosed in conjunction with the above specification.

In addition, while the preferred embodiment disclosed above takes the form of a pacemaker/cardioverter/defibrillator, the enhanced ability to distinguish between various tachyarrhythmias and the approved speed of detection provided by the present invention are also valuable and applicable to devices which are only capable of performing a subset of the various therapies discussed above in conjunction with FIG. 2. For example, the ability to accurately distinguish between slow and fast ventricular tachycardias would be valuable in an anti-tachycardia pacemaker, with or without the cardioversion pulse generator, to select between anti-tachycardia pacing therapies or between anti-tachycardia pacing and cardioversion therapies. Similarly, the ability to distinguish between a fast ventricular tachycardia and Ventricur fibrillation is valuable in an implantable cardioverter defibrillator, even if the cardiac pacing function is omitted, for example, as in the currently available CPI AICD implantable cardioverter defibrillators. It should further be kept in mind that while the therapies described for delivery in response to detection of the various arrhythmias discussed are all disclosed in the context of electrical therapies, it is possible that the invention may be embodied in the form of an implantable drug dispenser, wherein one or more of the anti-tachycardia therapies takes the form of injection of a drug locally into the heart or systemically to treat the detected arrhythmia. As such, the above disclosure should be taken merely as an example of an embodiment of the present invention, rather than limiting, when reading the claims which follow.

In conjunction with the above specification, I claim:

1. An apparatus for detection and treatment of arrhythmias, comprising:

means for sensing depolarizations of a patient's heart;

means for measuring intervals separating successive depolarizations of said patient's heart;

means for defining first and second adjacent, non-overlapping interval ranges and for defining a third interval range overlapping said first and second interval ranges;

means for determining numbers of said measured intervals falling within said first, second and third interval ranges;

first means for detecting an arrhythmia when the number of said measured intervals falling within said first interval range equals a first predetermined value;

second means for detecting an arrhythmia when the number of said intervals within said second interval range equals a second predetermined value;

means responsive to the detection of the arrhythmia by said first detecting means, for identifying the arrhythmia detected, comprising means for determining a number of said intervals falling within said third interval range within a series of said measured intervals preceding detection of said arrhythmia by said first detecting means and for identifying occurrence of a first arrhythmia in response to said number of intervals occurring within said series of intervals and falling within said third predetermined interval range being less than a third predetermined value and for identifying a second arrhythmia in response to said number of intervals occurring within said series of intervals and falling within said third interval range being greater than or equal to said third predetermined value;

means for delivering at least two types of arrhythmia therapies; and means responsive to said identifying means for selecting and triggering delivery of one of said arrhythmia therapies.

2. An apparatus according to claim 1 wherein said second interval range comprises intervals less than in said first interval range and wherein said third interval range comprises intervals greater than a predetermined interval duration within said second interval range and wherein said identifying means comprises means for identifying fibrillation in response to said number of intervals occurring within said series of measured intervals preceding detection of said arrhythmia by said first detecting means and falling within said third predetermined interval range being less than said third predetermined value and for identifying a fast ventricular tachycardia in response to said number of intervals occurring within said series of measured intervals preceding detection of said arrhythmia by said first detecting means and falling within said third interval range being greater than or equal to said third predetermined value.

3. An apparatus according to claim 1 wherein said second interval range comprises intervals less than in said first interval range and wherein said third interval range comprises intervals less than a predetermined interval duration within said first interval range and wherein said identifying means comprises means for identifying a slow tachycardia in response to said number of intervals occurring within said series of measured intervals preceding detection of said arrhythmia by said first detecting means and falling within said third predetermined interval range being less than said third predetermined value and for identifying slow ventricular tachycardia in response to said number of measured intervals occurring within said series of intervals preceding detection of said arrhythmia by said first detecting means and falling within said third interval range being greater than or equal to said third predetermined value.

4. An apparatus according to claim 1 or claim 2 or claim 3 wherein said means for sensing depolarizations comprises means for sensing depolarizations of said patient's ventricle.

5. An apparatus for detection and treatment of arrhythmias, comprising:

means for sensing depolarizations of a patient's heart;

means for measuring intervals separating successive depolarizations of said patient's heart;

means for defining first and second interval ranges corresponding to first and second arrhythmias;

means for defining a third interval range, overlapping said first interval range and indicative of a third arrhythmia;

means for determining numbers of said measured intervals falling within said first and second interval ranges;

means for detecting an arrhythmia when a sum of said numbers of said measured intervals falling within said first and second interval ranges equals a first predetermined value;

means for determining numbers of said measured intervals in said first and second interval ranges, within a first series of measured intervals preceding detection of said arrhythmia;

means responsive to the detection of said arrhythmia by said detecting means, for provisionally identifying said first arrhythmia in response to relative values of said numbers of intervals in said first and second interval ranges, within said first series of measured intervals;

means for confirming the provisional identification of said first arrhythmia, comprising means for determining a number of intervals within a second series of said measured intervals preceding detection of said arrhythmia and means for identifying the occurrence of said first arrhythmia in response to the number of intervals occurring within said second series of measured intervals and falling within said third predetermined interval range being less than a second predetermined value and for identifying said third arrhythmia in response to the number of intervals occurring within said second series of measured intervals and falling within said third interval range being greater than or equal to said second predetermined value;

means for delivering at least two types of arrhythmia therapies; and means responsive to said identifying means for selecting and triggering delivery of one of said arrhythmia therapies.

6. An apparatus according to claim 5 wherein said second interval range comprises intervals less than in said first interval range and wherein said third interval range comprises intervals greater than said predetermined interval duration within said second interval range and wherein said confirming means comprises means for identifying fibrillation in response to said number of intervals occurring within said second series of intervals and falling within said third predetermined interval range being less than a said second predetermined value and for identifying a fast ventricular tachycardia in response to said number of intervals occurring within said second series of intervals and falling within said third interval range being greater than or equal to said second predetermined value.

7. An apparatus according to claim 5 wherein said second interval range comprises intervals less than in said first interval range and wherein said third interval range comprises intervals less than said predetermined interval duration within said first interval range and wherein said confirming means comprises means for identifying a slow tachycardia in response to said number of intervals occurring within said second series of intervals and falling within said third predetermined interval range being less than said second predetermined value and for identifying slow ventricular tachycardia in response to said number of intervals occurring within said second series of intervals and falling within said third interval range being greater than or equal to said second predetermined value.

8. An apparatus according to claim 5 or claim 6 or claim 7 wherein said means for sensing depolarizations comprises means for sensing depolarizations of said patient's ventricle.

9. An apparatus for detection and treatment of arrhythmias, comprising:
means for sensing depolarizations of a patient's heart;
means for measuring intervals separating successive depolarizations of said patient's heart;
means for defining first and second interval ranges corresponding to first and second arrhythmias;
means for determining numbers of said measured intervals falling within said first and second interval ranges;
means for detecting an arrhythmia in response to a sum of the numbers of said measured intervals falling within said first and second interval ranges equalling a first predetermined value and the number of intervals in said second interval range and falling within a first series of preceding intervals being greater than or equal to a second predetermined value.

10. Apparatus according to claim 9 further comprising:
means for determining numbers of said measured intervals intervals in said first and second interval ranges, within a second series of measured intervals preceding detection of said arrhythmia; and
means responsive to detection of an arrhythmia by said detecting means, for provisionally identifying said first arrhythmia in response to relative values of said numbers of intervals in said first and second interval ranges within said second series of measured intervals preceding said detection of said arrhythmia.

11. Apparatus according to claim 10 further comprising:
means for identifying a third range of intervals overlapping said first range of intervals;
means for determining numbers of said measured intervals intervals in said third interval range within a third series of measured intervals preceding detection of said arrhythmia; and
means responsive to provisional identification of said first arrhythmia for confirming said provisional identification of said first arrhythmia in response to said number of intervals occurring within said third second series of intervals preceding detection of said arrhythmia and falling within said third predetermined interval range being less than a third predetermined value and for identifying a second arrhythmia in response to said number of intervals occurring within said third series of intervals and falling within said third interval range being greater than or equal to said third predetermined value.

12. An apparatus for detection and treatment of arrhythmias, comprising:
means for sensing depolarizations of a patient's heart;
means for measuring intervals separating successive depolarizations of said patient's heart;
means for defining first and second adjacent, non-overlapping interval ranges corresponding to first and second arrhythmias and for defining a third interval range overlapping said first and second interval ranges, corresponding to a third arrhythmia;
first means for provisionally detecting the occurrence of said first arrhythmia as a function of said measured intervals;
second means for detecting the occurrence of said second arrhythmia as a function of said measured intervals;
means responsive to the provisional detection of said first arrhythmia by said first detecting means, for identifying the type of arrhythmia detected, comprising means for determining the number of said intervals falling within said third interval range within a series of a said measured intervals preceding detection of said arrhythmia by said first detecting means and means for identifying the occurrence of said first arrhythmia in response to said number of intervals occurring within said series of intervals and falling within said third predetermined interval range being less than a predetermined value and for identifying said third arrhythmia in response to said number of intervals occurring within said series of intervals and falling within said third interval range being greater than or equal to said predetermined value;
means for delivering at least two types of arrhythmia therapies; and
means responsive to said identifying means for selecting and triggering delivery of one of said arrhythmia therapies.

13. An apparatus according to claim 12 wherein said second interval range comprises intervals less than in said first interval range and wherein said third interval range comprises intervals greater than a predetermined interval duration within said second interval range and wherein said identifying means comprises means for identifying fibrillation in response to said number of intervals occurring within said series of measured intervals preceding detection of said arrhythmia and falling within said third predetermined interval range being less than said predetermined value and for identifying a fast ventricular tachycardia in response to the number of intervals occurring within said series of measured intervals preceding detection of said arrhythmia and falling within said third interval range being greater than or equal to said predetermined value.

14. An apparatus according to claim 12 wherein said second interval range comprises intervals less than in said first interval range and wherein said third interval range comprises intervals less than a predetermined interval duration within said first interval range and wherein said identifying means comprises means for identifying a slow tachycardia in response to said number of intervals occurring within said series of measured intervals preceding detection of said arrhythmia and falling within said third predetermined interval range being less than said predetermined value and for identifying slow ventricular tachycardia in response to said number of measured intervals occurring within said series of intervals preceding detection of said arrhythmia and falling within said third interval range being greater than or equal to said predetermined value.

* * * * *